United States Patent [19]

Mylchreest et al.

[11] Patent Number: 5,122,670
[45] Date of Patent: Jun. 16, 1992

[54] MULTILAYER FLOW ELECTROSPRAY ION SOURCE USING IMPROVED SHEATH LIQUID

[75] Inventors: Iain C. Mylchreest, Sunnyvale; Mark E. Hail, Fremont, both of Calif.

[73] Assignee: Finnigan Corporation, San Jose, Calif.

[21] Appl. No.: 702,235

[22] Filed: May 17, 1991

[51] Int. Cl.⁵ .............................................. H01J 49/10
[52] U.S. Cl. .................................. 250/423 R; 250/281; 250/282; 250/288
[58] Field of Search ........... 250/423 R, 288 R, 288 A, 250/281, 282; 204/299 R

[56] References Cited

U.S. PATENT DOCUMENTS

| | | | |
|---|---|---|---|
| 4,861,988 | 8/1989 | Henion et al. | 250/288 A |
| 4,885,076 | 12/1989 | Smith et al. | 204/299 R |
| 4,935,624 | 6/1990 | Henion et al. | 250/288 A |
| 4,977,785 | 12/1990 | Willoughby et al. | 73/863.12 |
| 4,982,097 | 1/1991 | Stivon et al. | 250/288 A |
| 4,994,165 | 2/1991 | Lee et al. | 204/299 R |

Primary Examiner—Jack I. Berman
Assistant Examiner—Kiet T. Nguyen
Attorney, Agent, or Firm—Flehr, Hohbach, Test, Albritton & Herbert

[57] ABSTRACT

An electrospray ion source in which the liquid sample is sheathed with a sheath liquid which reduces the formation of water droplets and minimizes formation of high energy neutrals, resulting in improved signal-to-noise ratios.

2 Claims, 2 Drawing Sheets

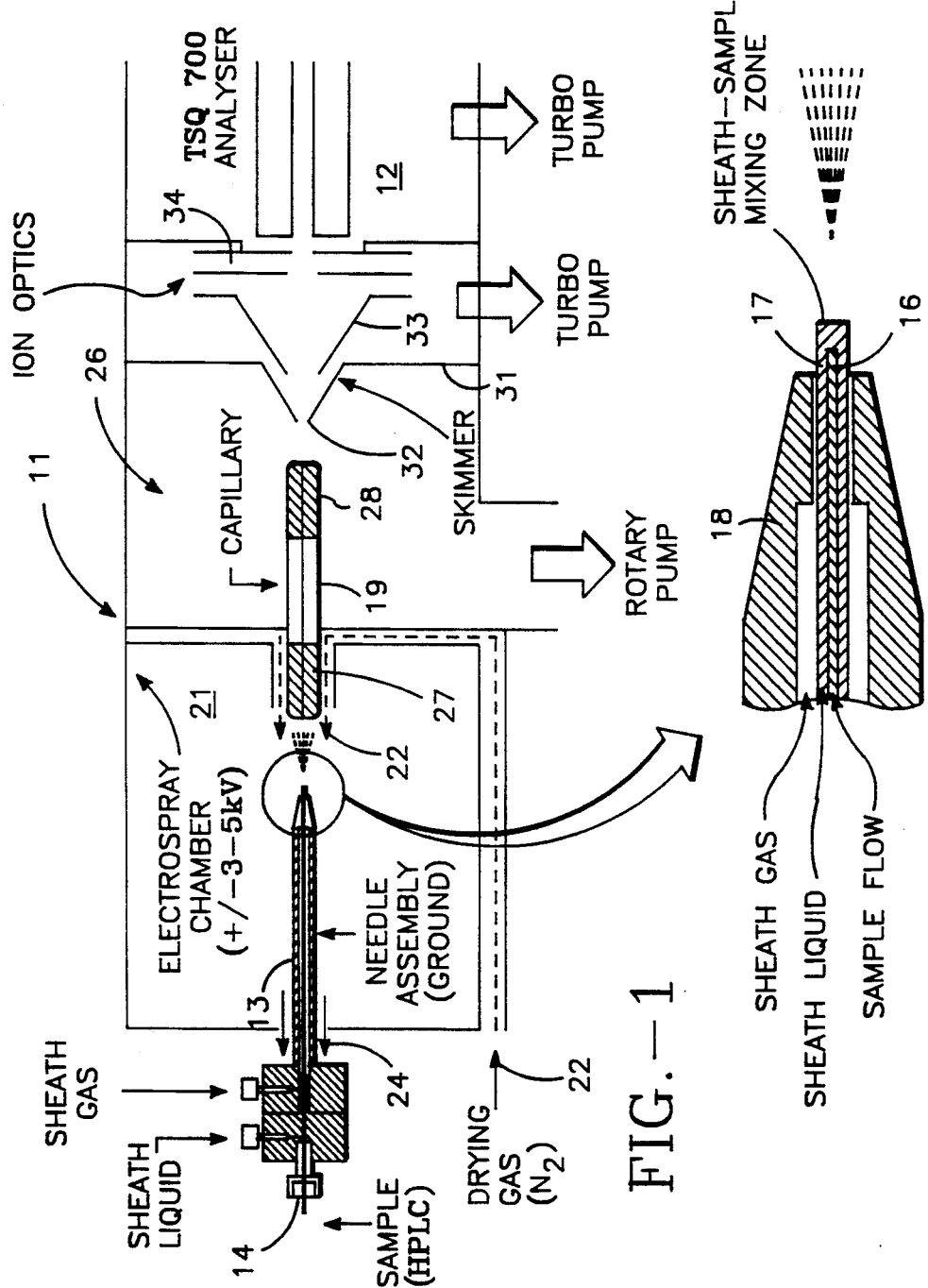

MULTILAYER FLOW ELECTROSPRAY ION SOURCE USING IMPROVED SHEATH LIQUID

BRIEF DESCRIPTION OF THE INVENTION

This invention relates generally to electrospray ion sources and more particularly to sources having reduced neutral noise.

BACKGROUND OF THE INVENTION

The electrospray process consists of flowing sample liquid through a small tube or capillary which is maintained at a high voltage with respect to a nearby surface. The liquid is dispersed into fine electrically charged droplets or by the voltage gradient of the tip of the capillary. The ionization mechanism involves the desorption at atmospheric pressure of ions from the fine electrically charged droplets. In many cases a heated gas is flowed in counter-current to the electrospray to enhance dissolution of the electrospray droplets. The ions created by the electrospray are then mass analyzed in a mass analyzer such as a mass spectrometer.

Under the appropriate conditions, the electrospray resembles a symmetrical cone consisting of a very fine mist (or fog) of droplets (ca. 1 $\mu$m in diameter). Excellent sensitivity and ion current stability can be obtained if the fine mist is produced. Unfortunately, the electrospray "quality" is highly dependent on the bulk properties of the solution being analyzed. The most important of which are surface tension and conductivity. A poor quality electrospray may contain larger droplets ($>10$ $\mu$m diameter) or a non-dispersed droplet stream.

The use of sheath liquid and a focusing gas are often used to insure stable sprays when electrospraying high aqueous content sample solutions. U.S. Pat. Nos. 4,977,785; 4,885,076, and copending patent application Ser. No. 575,183 describe electrospray ion sources including a sheathing liquid. The system described in said copending application uses a multilayer flow needle assembly which provides stable ion currents over a wide range of solution conditions (e.g., pH, conductivity, and aqueous content). The multilayer flow needle consists of a central tube for sample introduction, a second concentric tube for sheath liquid introduction, and a third concentric tube for gas flow addition. The primary purpose of the liquid sheath is to reduce the surface tension of the eluent stream in order to allow electrospray compatibility with solutions of high aqueous content. The concentric gas flow is important in that it improves ion current stability and sensitivity when solutions of high conductivity are electrosprayed. The sheath flow can result in the production of undesirable neutral noise in the mass spectrometer.

The neutrals are apparently caused by droplets which are directed through the ESI atmosphere/vacuum interface by the sheath gas flow. It is believed that the droplets cool as they enter vacuum and eventually freeze, forming tiny ice pellets. These particles are accelerated by the free jet expansion to supersonic velocities. In the free jet expansion, the particles attain enough kinetic energy to produce secondary ions when they impinge upon a surface. This results in intense noise "spikes" at the detector of the mass spectrometer.

OBJECTS AND SUMMARY OF THE INVENTION

It is a general object of this invention to provide an ion source and method in which noise from high velocity water droplets or particles is minimized It is another object of the invention to provide an ion source and method in which a sheath liquid having ion surface tension miscible in water and with a boiling point higher than water is used to minimize particulate formations.

The foregoing and other objects of this invention are achieved in a sheathed flow electrospray source by using a sheathing liquid which has a low surface tension, is miscible with water and has a boiling point higher than water.

BRIEF DESCRIPTION OF THE DRAWINGS

The foregoing and other objects of the invention will be more clearly understood from the description to follow when read in conjunction with the accompanying drawings of which:

FIG. 1 shows an electrospray ion source coupled to an analyzing region via a capillary tube;

FIG. 2 is an enlarged view of the region 2—2 of FIG. 1;

DETAILED DESCRIPTION OF THE INVENTION

Figure 3:
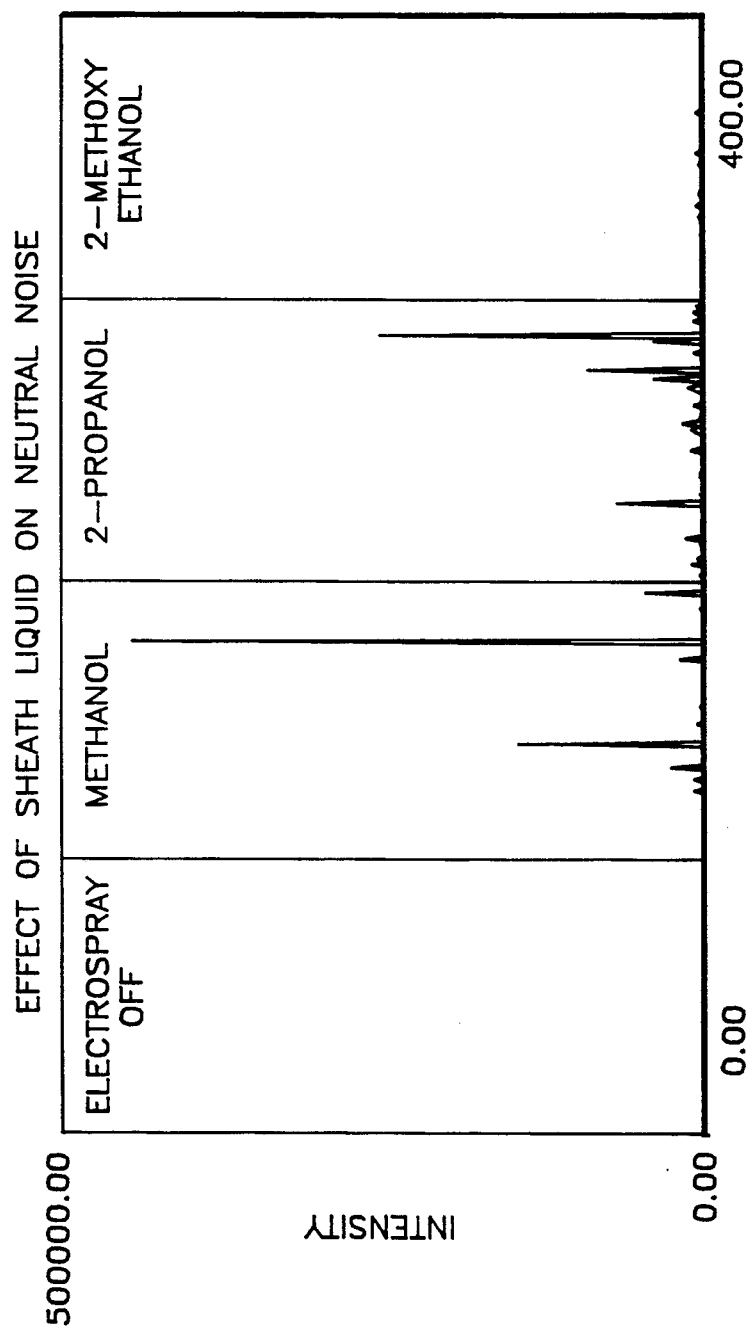
FIG. 3 shows the effect of sheath liquid on neutral noise.

Referring to FIG. 1, an electrospray ion source 11 is schematically shown as associated with an analyzer chamber 12. The source includes an input needle 13 into which a liquid sample 14 is introduced.

Referring particularly to FIG. 2, the needle includes an inner tube 16 in which the liquid sample is introduced. Surrounding the tube is a second tube 17 which defines with the first tube an annular region through which a sheath liquid is introduced for mixing with the sample liquid. An outer tube 18 forms a second annulus through which a focusing gas is introduced to focus the droplets as they exit the needle towards a capillary tube 19. As previously explained, the needle, or capillary, is maintained at a high voltage with respect to the nearby surfaces forming the ionization chamber 21 and as the liquid is dispersed, the droplets or particles are charged by the voltage gradient at the tip of the capillary. The ionization mechanism involves the desorption at atmospheric pressure of ions from the fine electrically charged particles. A counter-flow of gas indicated by the arrow 22 enhances the desorption process. The gas flows through a chamber 23 past the end of the capillary 19 and exits the ionization chamber 21 as indicated schematically at 24.

A chamber 26 maintained at a lower pressure than the atmospheric pressure of the chamber 21 communicates with the ionization chamber via the capillary tube 19. Due to the differences in pressure, ions and gas are caused to flow through the capillary 19 into the chamber 26. A voltage gradient is formed along the insulated capillary by applying voltages between conductive sleeves 27 and 28.

The end of the capillary is opposite a skimmer 31 which separates the low pressure region 26 from a lower pressure region in the analyzer 12. The skimmer includes a central orifice or aperture 32 which normally is aligned with the axis of the bore of the capillary. The skimmer is followed by ion optics which may comprise a second skimmer 33 and lenses 34, which direct ions into the analyzing chamber and into a suitable analyzer.

As described above, the undesolvated droplets or particles flow into the capillary and acquire kinetic energy which allows them to pass through the skimmer aperture 32 into the lens region including skimmer 33 and lenses 34. These droplets or particles impact on the surfaces of the skimmer 33 or the lenses 34 and create secondary ions. These ions are random and find their way into the detector and cause noise to be observed at the detector, thereby decreasing the signal-to-noise level and producing electronic spikes in the mass spectrum.

In accordance with this invention, the sheath liquid is selected to have properties which minimize the formation of water droplets which find their way into the low pressure analyzing region of the mass spectrometer. The properties which we have found to be important in good performance of a liquid chromatograph/mass spectrometer are:

First, the sheath liquid must have relatively low surface tension to allow compatibility with solutions containing high percentages of water. Second, the sheath liquid must be miscible in water, as well as methanol and acetonitrile (the commonly used LC solvents). Finally, the sheath liquid must have a boiling point higher than that of water. This property is important in minimizing the neutral noise produced by the system. Solvents that are too volatile are prematurely evaporated from the droplets, resulting in droplets containing high percentages of water. Since these droplets have high surface tension, they are not easily broken up into smaller droplets and are likely to create neutral noise.

The solvent 2-methoxyethanol possesses all the desirable properties listed above. A comparison of the neutral noise output obtained with three different sheath liquids is shown in FIG. 3. This figure demonstrates that both the frequency as well as the intensity of the noise events are dramatically reduced with 2-methoxyethanol. An additional benefit of the use of this solvent as a sheath liquid is that signal response is increased (two to three times) when used with mobile phases containing 0.1% trifluoroacetic acid (TFA).

Thus, there has been provided a sheath liquid for reducing neutral noise in an electrospray caused by water droplets.

What is claimed:

1. An electrospray ion source of the type which includes an ionization chamber into which sheathed liquid sample is introduced and an adjacent low pressure region with means communicating between the ionization chamber and the lower pressure region whereby ions and gases in said ionization chamber flow into said region, the improvement comprising
   using a sheath liquid which has low surface tension, is compatible with liquid samples having high water percentage, is miscible with water, methanol and acetonitrile, and has a boiling point higher than water.

2. An electrospray ion source as in claim 1 in which said sheath liquid is 2-methoxyethanol.

* * * * *